US00PP29779P2

(12) United States Plant Patent
Dirr et al.

(10) Patent No.: US PP29,779 P2
(45) Date of Patent: Oct. 30, 2018

(54) ***DISTYLIUM* PLANT NAMED 'PIIDIST-VI'**

(50) Latin Name: ***Distylium myricoides* x *Distylium racemosum***
Varietal Denomination: PIIDIST-VI

(71) Applicant: Bailey Nurseries Inc., Newport, MN (US)

(72) Inventors: Michael A. Dirr, Bogart, GA (US); Rhonda Helvick, Madison, GA (US); Oren McBee, Bishop, GA (US); Mark Griffith, Watkinsville, GA (US); Jeff Beasley, Lavonia, GA (US)

(73) Assignee: BAILEY NURSERIES INC., Newport, MN (US)

( * ) Notice: Subject to any disclaimer, the term of this patent is extended or adjusted under 35 U.S.C. 154(b) by 59 days.

(21) Appl. No.: 15/530,609

(22) Filed: Feb. 6, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan Beth McCormick Ewoldt
*Assistant Examiner* — Karen M Redden
(74) *Attorney, Agent, or Firm* — Penny J. Aguirre

(57) ABSTRACT

A new cultivar of *Dystilium* hybrid plant named, 'PIIDIST-VI', that is characterized by its compact, freely branched, mounded, and evergreen plant habit, its small, ovate-lanceolate shaped leaves that are green with a hint of red-purple in color when young and dark green in color when mature, and its good cold hardiness.

2 Drawing Sheets

Botanical classification: *Distylium myricoides* x *Distylium racemosum.*

Varietal denomination: 'PIIDIST-VI'.

BACKGROUND OF THE INVENTION

The present invention relates to a new and distinct cultivar of *Distylium mycricoides* x *Distylium racemosum* and will be referred to hereafter by its cultivar name, 'PIIDIST-VI'. 'PIIDIST-VI' represents a new *Distylium*, an evergreen shrub grown for landscape use.

The new cultivar of *Distylium* arose from a breeding program conducted by the Inventors in Watkinsville, Ga. 'PIIDIST-VI' originated as a seedling that arose from seed planted from the open pollination of *Distylium* hybrid 'PIIDIST-II' (U.S. Plant Pat. No. 24,409). 'PIIDIST-VI' was selected as a single unique plant in summer of 2013 from amongst the resulting seedlings.

Asexual propagation of the new cultivar was first accomplished by semi-hardwood stem cuttings by one of the Inventors in Watkinsville, Ga. in 2014. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PIIDIST-VI' as a unique cultivar of *Distylium.*

1. 'PIIDIST-VI' exhibits a compact, freely branched, mounded, and evergreen plant habit.
2. 'PIIDIST-VI' exhibits small, ovate-lanceolate shaped leaves that are green with a hint of red-purple in color when young and dark green in color when mature.
3. 'PIIDIST-VI' exhibits good cold hardiness.

'PIDIST-II', the female parent of 'PIIDIST-VI', differs from 'PIIDIST-VI' in having a more spreading plant habit and in having leaves that are maroon-purple when young and dark blue-green when mature. 'PIIDIST-VI' can be most closely compared to the *Distylium* cultivars 'PIIDIST-I' (U.S. Plant Pat. No. 24,410) and PIIDIST-III (U.S. Plant Pat. No. 25,304). 'PIDIST-I' differs from 'PIIDIST-VI' in having a more upright plant habit and in having young foliage that is yellow-green in color. 'PIIDIST III' differs from 'PIIDIST-VI' in having a rounded to spreading plant habit and in having leaves that are bronze-purple when young and dark bluish green when mature.

BRIEF DESCRIPTION OF THE DRAWINGS

The accompanying colored photographs illustrate the overall appearance and distinct characteristics of the new *Distylium*. The photographs were taken of a four-year-old plant as grown in the ground in full sun in Watkinsville, Ga.

The photograph in FIG. 1 provides a side view of the plant habit of 'PIIDIST-VI'.

Figure 1:
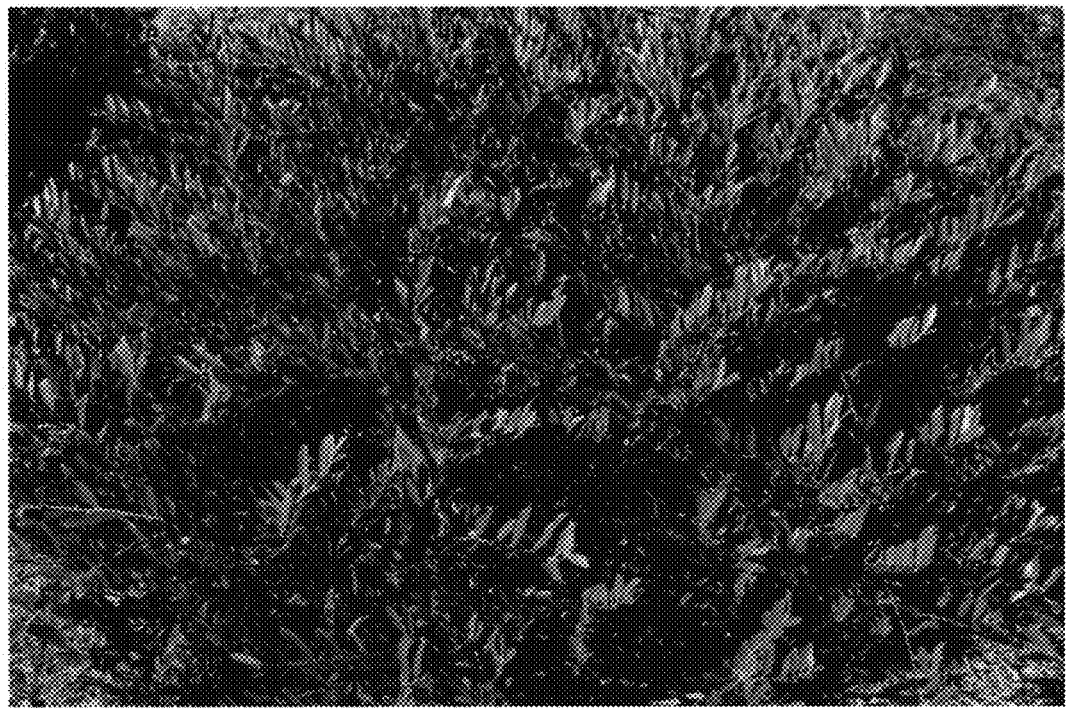
Figure 2:
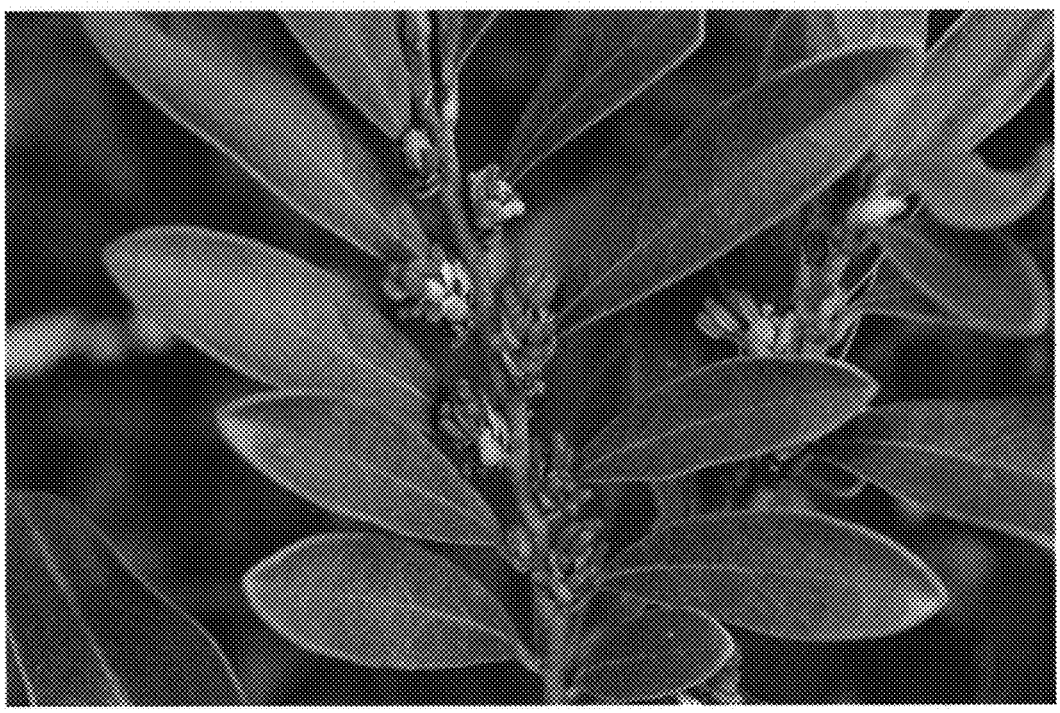

The photograph in FIG. 2 provides a close-up view of the leaves and inflorescences of 'PIIDIST-VI'.

The colors in the photographs are as close as possible with the photographic and printing technology utilized and the color values cited in the Detailed Botanical Description accurately describe the colors of the new *Distylium.*

DETAILED BOTANICAL DESCRIPTION

The following is a detailed description of four-year-old plants as grown in the ground in full sun in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late winter, from January to February in Watkinsville, Ga.

*Plant type*.—Evergreen shrub.

*Plant habit*.—Compact, well-branched, mounded.

*Height and spread*.—An average of 61 cm in height and 1.52 m in spread as a 4 year-old plant in the landscape.

*Hardiness*.—At least in U.S.D.A. Zones 7 to 9.

*Diseases and pests*.—No susceptibility or resistance to pests or diseases has been observed.

*Root description*.—Fibrous, well-branched and extensive, 156A in color.

*Propagation*.—Semi-hardwood stem cuttings.

*Time required for root development*.—An average of six weeks for root initiation in the summer at 32° C. with a young rooted plant produced in about three months at 32° C.

*Growth rate*.—Moderate.

Branch description:

*Branch color*.—First year; 138A, second year and older; 199B to 199C, older bark and trunk; 199A.

*Branch size*.—First year; an average of 16 cm in length and 2 mm in diameter; second year and older; an average of 60 cm in length and 3.5 mm in diameter, trunk; an average of 7 cm in diameter at the soil.

*Stem shape*.—Rounded.

*Stem surface*.—First year; Finely pubescent and slightly lenticellate with lenticels an average of 1 mm in diameter and N199B in color, second year and older; glabrous and smooth, older bark and trunk; none exfoliating and is densely lenticellate with lenticels about 1 mm in diameter and N199B in color.

*Stem strength*.—First year; flexible, second year and older; easily broken.

*Branching habit*.—Freely branching.

Foliage description:

*Leaf division*.—Simple.

*Leaf attachment*.—Petiolate.

*Leaf arrangement*.—Alternate.

*Leaf shape*.—Elliptic to lanceolate.

*Leaf size*.—An average of 4 cm in length and 1.5 cm in width.

*Leaf apex*.—Acute.

*Leaf base*.—Cuneate.

*Leaf number*.—An average of 26 leaves per branch 12 cm in length.

*Leaf surface*.—Upper and lower surfaces; smooth, thick, and coriaceous.

*Leaf venation*.—Pinnate, color; young and mature leaves upper and lower surfaces; midrib 137A and lateral veins 144A.

*Leaf margin*.—Entire and occasionally undulate.

*Leaf color*.—Young leaves; upper surface 137A suffused with 64A and lower surface 144A, mature leaves; upper surface N137A and lower surface 144A.

*Leaf bud*.—An average of 2 mm in length and 1 mm in width, ovoid in shape, surface covered with fused pubescent bud scales, N137A lightly suffused with 64A in color.

*Internode length*.—An average of 1.5 cm.

*Petiole*.—An average of 1 mm in diameter and 4 mm in length, rounded in shape, 199C in color, pubescent in surface.

Flower description:

*Inflorescence type*.—Short axillary racemes comprised of apetalous flowers with a 5-parted calyx.

*Inflorescence aspect*.—Upwards.

*Inflorescence size*.—An average of 2 cm in height and 1 cm in width.

*Flower quantity*.—An average of 2 flowers per inflorescence and about 7 inflorescences per lateral stem.

*Flower lastingness*.—An average of 1 week, self-cleaning.

*Flower aspect*.—Upwards.

*Flower type*.—Apetalous with showy stamens subtended by pubescent sepals.

*Flower size*.—About 1.1 cm in depth and 1 cm in diameter.

*Sepals*.—5, an average of 2.8 mm in width and 1.2 mm in length, ovate in shape, entire margin, acute apex, truncate to rounded base, upper and lower surfaces a blend between 157C and 161D in color and pubescent with hairs 165A in color.

*Peduncles*.—An average of 1.2 cm in length and 2 mm in diameter, rounded in shape, 146C in color with pubescence 165A in color.

*Pedicels*.—An average of 2 mm in length and 0.7 mm in diameter, rounded in shape, 146C in color with pubescence 165A in color.

Reproductive organs:

*Gynoecium*.—1 pistil, stigma; 2 per pistil, linear in shape, held above stamens, an average of 6 mm in length, 178B in color, style; an average of 3 mm in length, 146B in color, ovary; 2 per flower, superior, an average of 2 mm in length and diameter, 146B in color.

*Androcoecium*.—An average of 7 to 10 showy stamens per flower, an average of 5 mm in length, anthers; basifixed, an average of 2 mm in length and 1 mm in width, 185A in color, filament; an average of 3 mm in length and >1 mm in width, 146D in color, pollen is moderate in quantity and 158D in color.

*Fruit and seed*.—Fruit; two-valved capsule, beaked and woody containing 1 seed per valve, an average of 1 cm in length and 5 mm in width, 200C in color, seed; oblong to elliptical in shape, and average of 5 mm in length and 2 mm in width, N200A in color.

It is claimed:

1. A new and distinct cultivar of *Distylium* plant named 'PIIDIST-VI' as herein illustrated and described.

* * * * *